(12) United States Patent
Root

(10) Patent No.: US 6,782,630 B2
(45) Date of Patent: Aug. 31, 2004

(54) DEVICE AND METHOD FOR USE IN TAKING MOULDS OF FEET

(76) Inventor: Andrew Carl Root, Hopyard Farm, Lubbesthorpe, Enderby, Leicestershire LE9 SAF (GB)

( * ) Notice: Subject to any disclaimer, the term of this patent is extended or adjusted under 35 U.S.C. 154(b) by 0 days.

(21) Appl. No.: 09/918,582

(22) Filed: Jul. 31, 2001

(65) Prior Publication Data

US 2002/0100179 A1 Aug. 1, 2002

(30) Foreign Application Priority Data

Jan. 31, 2001 (GB) .............................. 0102389

(51) Int. Cl.⁷ ................................................ A61F 5/00
(52) U.S. Cl. .......................................... 33/515; 33/512
(58) Field of Search .......................... 33/515, 512, 333, 33/370, 371–3, 3 R, 6, 3 A–3 B; 600/587

(56) References Cited

U.S. PATENT DOCUMENTS

| | | | | |
|---|---|---|---|---|
| 743,663 A | * | 11/1903 | Scheidl ........................ | 602/39 |
| 3,020,909 A | * | 2/1962 | Stevens ...................... | 602/39 |
| 3,143,110 A | * | 8/1964 | Stryker ........................ | 602/39 |
| 3,908,643 A | * | 9/1975 | Bliss ........................... | 128/83 |
| 3,974,491 A | * | 8/1976 | Sipe ........................... | 340/272 |
| 4,261,348 A | * | 4/1981 | Hargadon ................... | 128/83 |
| 4,323,080 A | * | 4/1982 | Melhart ...................... | 128/774 |
| 4,443,005 A | * | 4/1984 | Sugarman et al. ............. | 5/651 |
| 4,771,548 A | * | 9/1988 | Donnery ..................... | 33/512 |
| 4,886,258 A | * | 12/1989 | Scott ............................ | 5/624 |
| 5,063,918 A | * | 11/1991 | Guhl .......................... | 602/40 |
| 5,678,448 A | * | 10/1997 | Fullen et al. ................. | 73/172 |
| 5,891,151 A | * | 4/1999 | Rivera-Esquerdo ...... | 606/105.5 |
| 5,908,397 A | * | 6/1999 | Tatum et al. .................. | 602/5 |

FOREIGN PATENT DOCUMENTS

| | | | |
|---|---|---|---|
| GB | 778604 | | 7/1957 |
| GB | 1512017 | | 5/1978 |
| GB | 0872225 A2 | * | 10/1998 |
| RU | 2020891 C1 | * | 10/1994 |
| RU | 2111729 C1 | * | 5/1998 |
| WO | PCT/AU84/00003 | | 7/1984 |

* cited by examiner

Primary Examiner—Christopher W. Fulton
Assistant Examiner—Tania C. Courson
(74) Attorney, Agent, or Firm—Young & Basile, P.C.

(57) ABSTRACT

A device and method is provided whereby application is made to at least part of the sole of a suitably positioned foot. The device (1) (FIGS. 1 and 2) comprises a member or plate (20) having a planar surface (21) for pressure application to the sole by a handle (28) and in one arrangement is hingedly mounted (22, 24, 26) about horizontal axes from a leg rest (10) which lies in use on a seat or couch for the patient. This enables the surface (21) to be brought against the sole and also tilted for required contact with the latter. The plate (20) is also shown mounted for angular movement about a vertical axis X for additional tilting of the surface (21). An electronic unit (30) on the plate (20) has an LCD display (32) for showing angles of tilt. With the surface (21) in appropriate contact the sole can be manually palpated or manipulated e.g. for contact of the surface (21) with metatarsal joints or points, and/or the subtalar joint palpated for the neutral condition etc. The required position of the surface (21) is maintained while molding material such as plaster of Paris (e.g. as a bandage) is applied to the sole and foot and allowed to set in providing a mold for use in the manufacture of orthoses. Alternatively, the plate may be simply hand held for similar operation. The planar surface may have buttons each for initial contact with a metatarsal point for indicator lamp operation when the metatarsal point lifts away. The handle may operate strain gauge means of the electronic unit to indicate application pressure at the LCD display.

10 Claims, 8 Drawing Sheets

DEVICE AND METHOD FOR USE IN TAKING MOULDS OF FEET

BACKGROUND OF THE INVENTION

This invention relates to a device and method for use in the taking of moulds or like three-dimensional impressions of feet.

Foot orthotics are an essential part of conservative orthopaedic treatment for correction of biomechanical abnormalities, congenital deformities and abnormal positions acquired through accident or disease processes. The taking of accurate plaster of Paris moulds or three-dimensional impressions of feet is a necessary part of the process of manufacture of foot orthotics.

At present, the plaster of Paris casts and three-dimensional impressions of feet are taken in the following positions:

With a patient sitting with the knee extended, or lying in a prone or supine position, the clinician palpates the subtalar joint to a neutral position with one hand, whilst the remaining hand applies dorsiflexory pressure to the fifth metatarsophalangeal joint or to the plantar surface of the webbing of the fourth and fifth toes.

Alternatively, with a patient sitting with the knee flexed, the foot is allowed to semi-weight bear whilst the clinician maintains the subtalar joint in a neutral position with one hand, as the plaster of Paris bandage or three-dimensional moulding material is placed around the foot and hardens.

A major problem with conventional methods of making casts and impressions of feet is their inherent lack of reproducibility. This can lead to the production of ill-fitting orthotics which may be uncomfortable and/or detrimental to the user.

SUMMARY OF THE INVENTION

There has now been devised a device and method for use in the taking of moulds and three-dimensional impressions of feet which overcome, or substantially mitigate, the above-mentioned or other disadvantages.

According to a first aspect of the invention, a device for use in the taking of a mould or impression of a foot comprises a generally planar member adapted for abutment with the sole of a patient's foot, and means by which the device may be held in any desired orientation.

According to a second aspect of the invention, a method of taking of a mould or impression of a foot comprises applying to the sole of the foot the planar member of a device as defined above, and holding the device in a desired orientation.

According to a third aspect of the invention, a device for use in the taking of a mould or impression of a foot comprises a generally planar member adapted for abutment with the sole of a patient's foot, and means for detecting angular displacement of the planar member, According to a fourth aspect of the invention, a method of taking of a mould or impression of a foot comprises applying to the sole of the foot the planar member of a device as defined above, and detecting the angular displacement of the planar member.

In a preferred embodiment, the device according to the invention is provided with angular measurement means and display means, by which angular displacement of the planar member from a datum position can be determined. In one preferred embodiment, such means may be electronic. In such a case, means for setting the display to zero to provide a datum are preferably provided. This means may be push button actuatable by the clinician, to facilitate measurement of a given angular displacement from the datum position. Alternatively, the angular measurement and display means comprises a Vernier scale arrangement.

The angular measurement means may comprise means by which movement in degrees of tilt in the frontal plane of the foot may be measured by mechanical and/or magnetic and/or rotational movement. The angular measurement means may, for instance, include means for detecting a reference and means for determining the position of the vertical plane in relation to that reference. The reference may comprise another part of the foot or leg, or may be an external reference such as magnetic north, a mechanical reference means, or may be provided by means of a gyroscope. A potentiometer may be provided which is rotated when the device is rotated, thereby changing the resistance of the potentiometer. The resultant change in voltage may, after suitable calibration, be converted by digital logic to an output value in degrees which is displayed, e.g. on a liquid crystal display. A separate moving axis may be added to the planar member or built into the planar member to act as a reference point, or a fixed point strapped to the leg or foot or otherwise fixed, e.g. to the patient's chair, may extend to the planar member.

The new device can be used with the patient seated with the knee extended, or with the patient lying in a prone or supine position.

The planar member may be hingedly connected to one or more further planar members to allow separate forefoot and rear foot movement and first ray movement of the foot to be detected.

The device according to the invention is advantageous primarily in that it facilitates more accurate taking of three dimensional impressions of feet, which is currently carried out manually holding the foot whilst the plaster hardens to form the cast. The accuracy of alignment may be within a single degree or better. The device provides greater stability whilst the mould is being taken and, in preferred embodiments, any movement of the patient's foot or the clinician's hand will be visibly seen on the liquid crystal display, enabling the position to be corrected. This is especially important when taking moulds of children's feet.

The device also reduces or eliminates the need for adding estimated amounts of intrinsic posting to the positive cast, which is time consuming and a major source of inaccuracy in the finished orthosis.

The device may be used for the manufacture of both foot orthoses and ankle/foot orthoses. The device can be used for a three-dimensional impression of a foot, when using impression materials or impression bagging materials which surround the foot, whilst the clinician can check the angular position of the foot at any time.

The device thus improves both the reproducibility and accuracy of three dimensional impressions of feet.

DESCRIPTION OF THE DRAWINGS

The invention will now be described, by way of example only, with reference to the accompanying drawings, in which.

DETAILED DESCRIPTION

Figure 1:
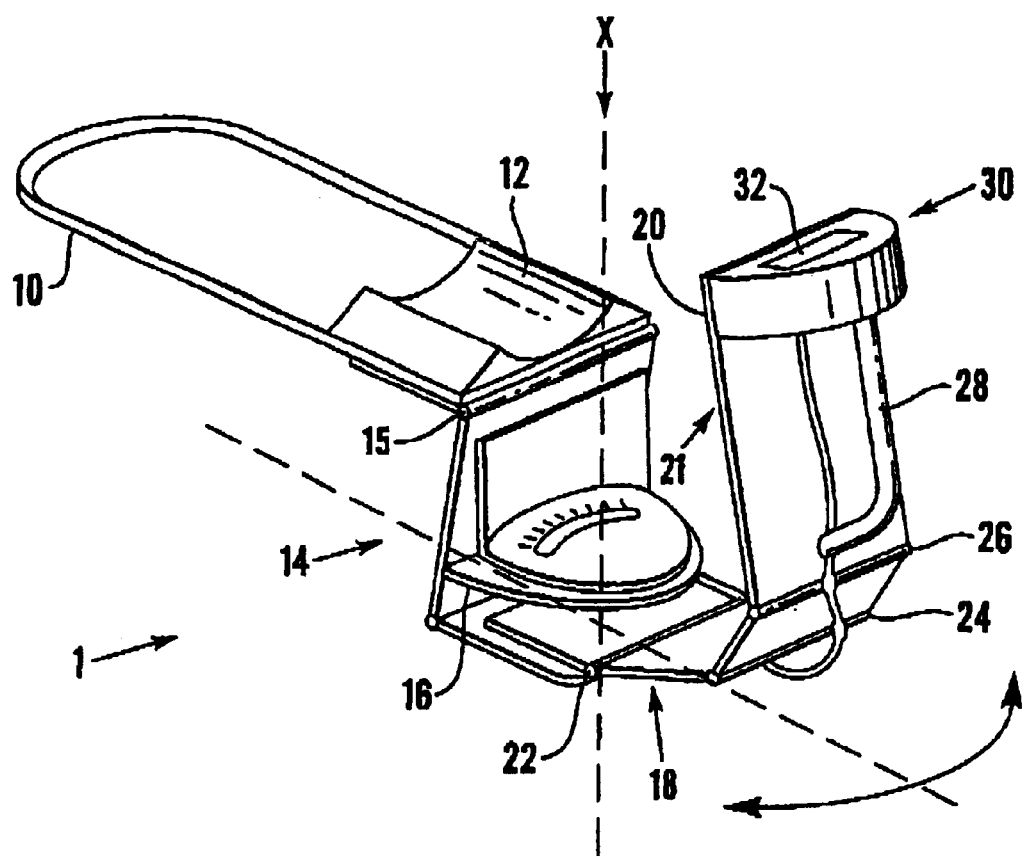
FIG. 1 is a perspective view of a preferred embodiment of a device according to the invention using electronic means to detect the tilt movement of the handle and plate.
Figure 2:
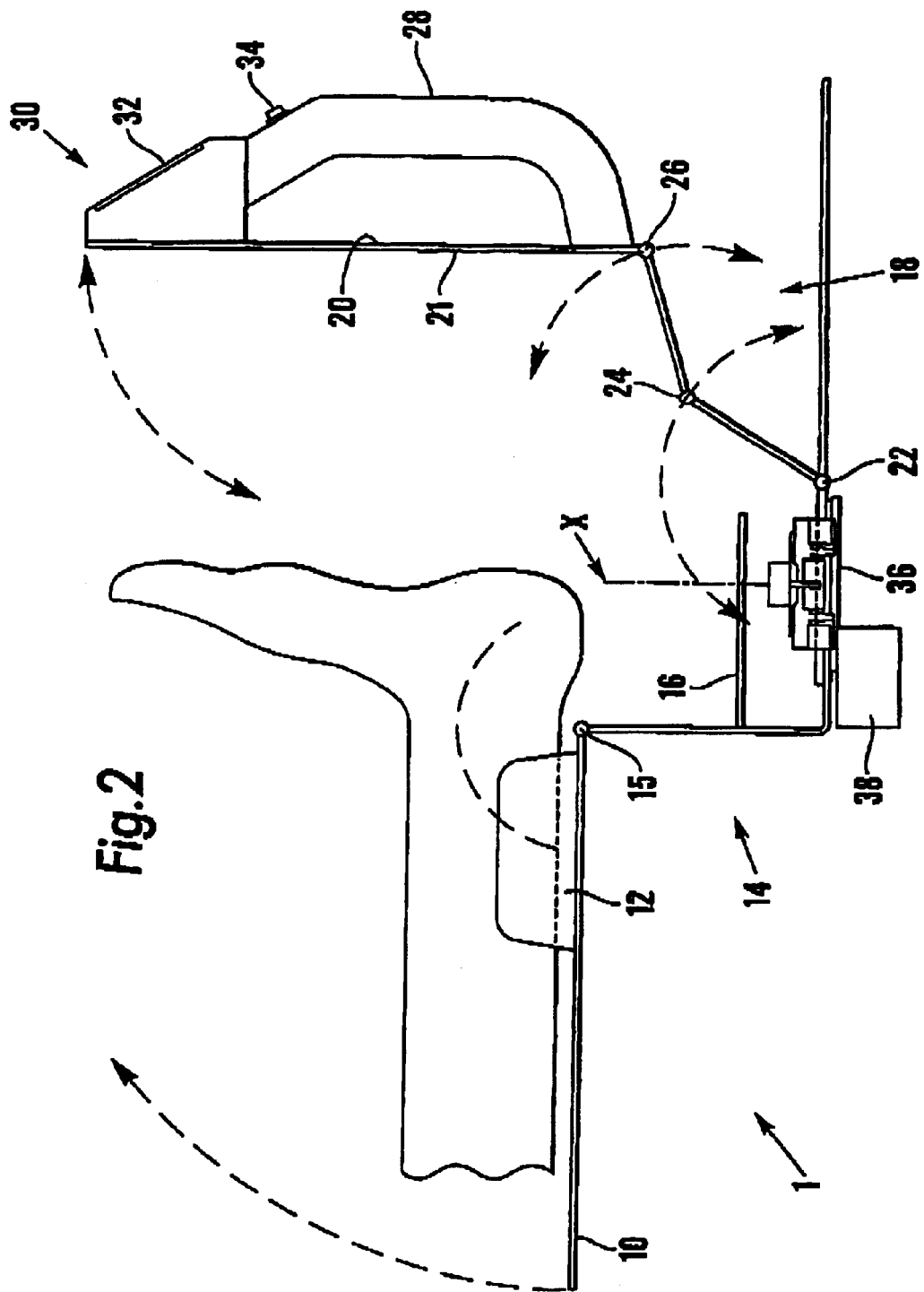
FIG. 2 is a schematic elevation of the device of FIG. 1.

Referring first to FIGS. 1 and 2, a device according to the invention is generally designated at 1. The device 1 comprises a leg rest 10 which, in use, is placed on the edge of the chair or couch on which a patient sits or lies, the patient's lower leg being supported by the rest 10 with the ankle and foot projecting beyond it. The front edge of the rest 10 is provided with a soft insert 12, which acts as a lower leg rest for the patients comfort.

The rest 10 has a downwardly directed front portion 14 on which a removable tray 16 is received. The front portion 14 is hingedly connected at 15 to the rest 10, to allow the device to be folded for ease of transport.

An articulated platform 18 is pivotally mounted at a lower level on the front portion 14 of the rest 10. Hence, the platform 18 can be rotated about a vertical axis X. The platform 18 carries a planar member in the form of a rigid plate 20 having a planar surface 21 which, in use, is brought into contact with the sole of a patient's foot, as described in detail below. Hinges 22, 24, 26 allow movement of the platform 18 about horizontal axes. A handle 28 is fitted to the plate 20 to facilitate manipulation. Mounted on the plate 20, above the handle 28 is an electronics unit 30 for measuring angular tilt of the plate 20. The unit 30 has a liquid crystal display 32, and a zero reset button 34 is incorporated into the handle 28. The button 34 is positioned so as to be operable by the thumb of a user's hand which grasps the handle 28.

In this embodiment, electronic means in the form of a potentiometer 36, positioned at the point of vertical pivotal attachment of the platform 18, to the front portion 14 is used to detect and measure movement of the platform 18 about the vertical axis X, this movement being indicative of the degree of side tilt of the plate 20 and planar surface 21 about the frontal plane of the foot. (The frontal or coronal plane is the longitudinal plane made by cutting lengthwise from side to side through head and body or body part alone the coronal suture of the skull or parallel to it. The frontal plane is at right angles to the sagittal plane.) A power pack 38 is attached to the underside of the front portion 14, so as to enable the device to be portably operated. The electronics unit involved, which will be described in more detail later, detects tilt of the plate 20 to 0.1 degree of accuracy, thus enabling the inversion/eversion of the foot to be monitored and closely controlled whilst the mould sets. The degree of correction can therefore be set using the digital readout at 32, which is indicative of the frontal plane angle of the foot.

The method for taking subtalar joint neutral casts using plaster of Paris or three-dimensional moulding materials will now be described.

The patient may be in a prone or supine position or sitting up with hip flexed and knee extended as the clinician prefers.

A plaster of Paris bandage is applied to the foot in the usual manner in preparation for the casting position and the patient told to relax the foot completely as the bandage application is completed.

In order to use the device 1, the rest 10 is placed on the patient's chair or couch and the patient's leg placed in position. The planar surface 21 of the hingedly mounted plate 20 is then brought into contact with the sole of the patient's foot, which is manipulated, essentially as described below. The tray 16 collects surplus casting material and is easily removed for cleaning (or may be a completely disposable item).

The planar surface 21 of the plate 20 (which may be referred to as a casting plate), is held against the plantar surface of the foot by the clinician, and dorsiflexory pressure applied to the handle 28. The clinician ensures that the plate 20 and the foot are both in line with the leg, then depresses the zero reset button 34 to set a datum position, readable on the display 32, from which the angle of tilt can be measured. The clinician's free hand may then simultaneously palpate the subtalar joint position required by inverting and everting the plate 20 by the required amount, as indicated on the display 32. The subtalar joint position is then held exactly by maintaining dorsiflexory pressure through the plate 20. The amount of dorsiflexory pressure applied through the handle 28 against the foot may be varied accordingly. The pressure may be applied to both rear foot and forefoot simultaneously or forefoot pressure only to prevent any soft tissue compression of the rear foot. If the forefoot does not become fully plantigrade with dorsiflexory pressure from the plate 20 the other hand can be removed from palpating the talonavicular joint and used to apply a downward force to the dorsum of the metatarsophalangeal joints thereby making the forefoot plantigrade with the planar surface 21 of the plate 20. The frontal plane angle of the foot is maintained at all times by checking the liquid crystal display.

The position is maintained until the plaster of Paris bandage hardens, so that the cast can then be removed without causing deformation of the plaster. If required, the casting procedure is then repeated on the other foot.

In a prone position, where lines have been drawn on the skin to bisect the posterior of the lower leg and to bisect the posterior of the calcaneum, the device 1 may be used to take the cast in either subtalar joint neutral position alone or heel vertical position, or by inverting/everting the planar surface 21 from subtalar joint neutral, the cast may be taken in the degree of varus/valgus correction required. With heel vertical prone casting, a separate 90° heel vertical marker (not shown) is added to the planar surface 21 (e.g. by means of a clip fitting on the plate 20) and simply aligned to a bisection line previously marked on the posterior of the calcaneum whilst applying dorsiflexory pressure via the plate 20. The thumb of the hand holding the handle 28 depresses the zero degree reset button 34 and in a varus foot the free hand applies downward pressure to the dorsum of the first metatarsophalangeal joint bringing it into contact with the planar surface 21. If the foot is in a plantigrade position against the dorsiflexory pressured planar surface 21 with the heel vertical marker aligned to the posterior bisection of the calcaneum, increased dorsiflexory pressure may be applied at once to both forefoot and rear foot simultaneously, or pressure may be applied to the forefoot only to prevent soft tissue compression to the plantar surface of the calcaneum, whilst the marker still maintains heel vertical position. The position is maintained until the plaster hardens or the three-dimensional moulding material has gone evenly around the foot and sets.

When requiring a mould with a degree of correction from subtalar joint neutral, e.g. 4° varas, subtalar joint neutral position is initially palpated with one hand palpating the talonavicular joint and the other hand inverting and everting the foot with the planar surface 21 applying a constant dorsiflexory force to the plantar surface of the foot until neutral position is palpated. The reset button 34 is then depressed. Then the planar surface 21 is moved in the frontal plane, increasing the height of the arch, to register e.g. 4° on the liquid crystal display 32. The foot has now been corrected by 4° and the cast will harden in 4° of varus correction. Pressure may then be increased to the forefoot by the planar surface 21 keeping the same frontal plane degree position, as displayed by the liquid crystal display 32, until the forefoot becomes plantigrade. Alternatively, the hand palpating the talonavicular joint may be removed (without altering the 4° position of the surface 21), allowing the apices of the index and third finger of the free hand to apply downward pressure inside the bandage to the dorsum of the first metatarsophalangeal joint, to bring the foot into a plantigrade position with the planar surface 21. The cast, when removed, will be in 4° of varus correction from subtalar joint neutral.

Figure 3:
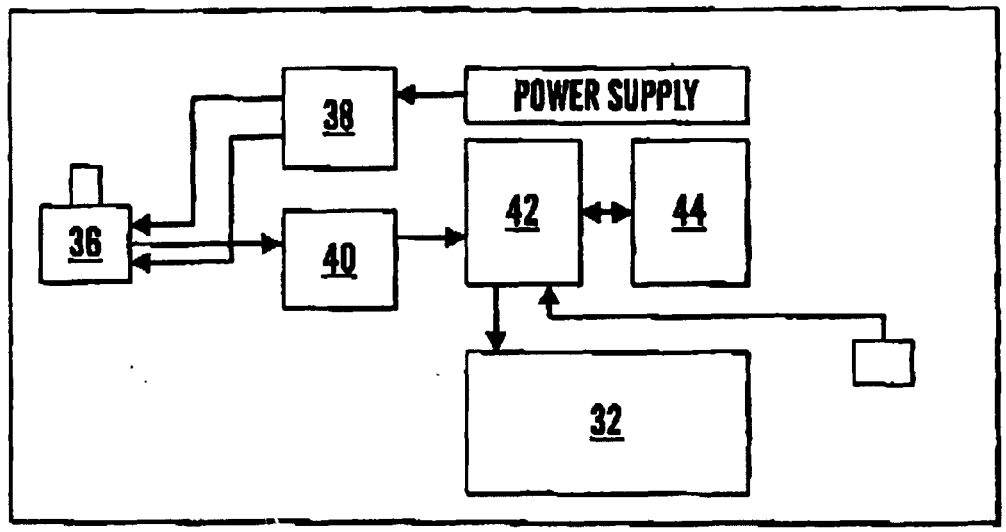
FIG. 3 shows the electronic circuitry involved in the embodiment of FIGS. 1 and 2.

FIG. 3 is a system block diagram of the electronics circuit used in the embodiment of FIGS. 1 and 2. The angular displacement of the planar surface 21 (FIGS. 1 and 2) is measured by the potentiometer 36. The potentiometer 36 is supplied with a reference voltage 38 across its end terminals and a voltage appears at the potentiometer wiper terminal whose value represents the angle to be measured.

This voltage is measured by an Analogue to Digital Converter (ADC) 40 which is controlled by a microprocessor 42. The microprocessor 42 reads the voltage and converts it to an angle using a simple proportional calculation. This reading is the uncorrected angle (represented by the symbol Au in FIG. 4) of the potentiometer 36. Since the potentiometer 36 has inherent inaccuracies due to its physical characteristics, the microprocessor 42 corrects this reading Au by applying corrections stored in the EEPROM 44 (Electrically Erasable Programmable Read Only Memory). These corrections are calculated during the production calibration phase of the device; by comparing the reading Au against a known accurate reference angle measuring device (not shown). These comparisons are made typically every 5 degrees mid the corrections are stored in the EEPROM. EEPROM memory is non-volatile, i.e. its data is retained even when power is removed form the circuit.

Figure 4:
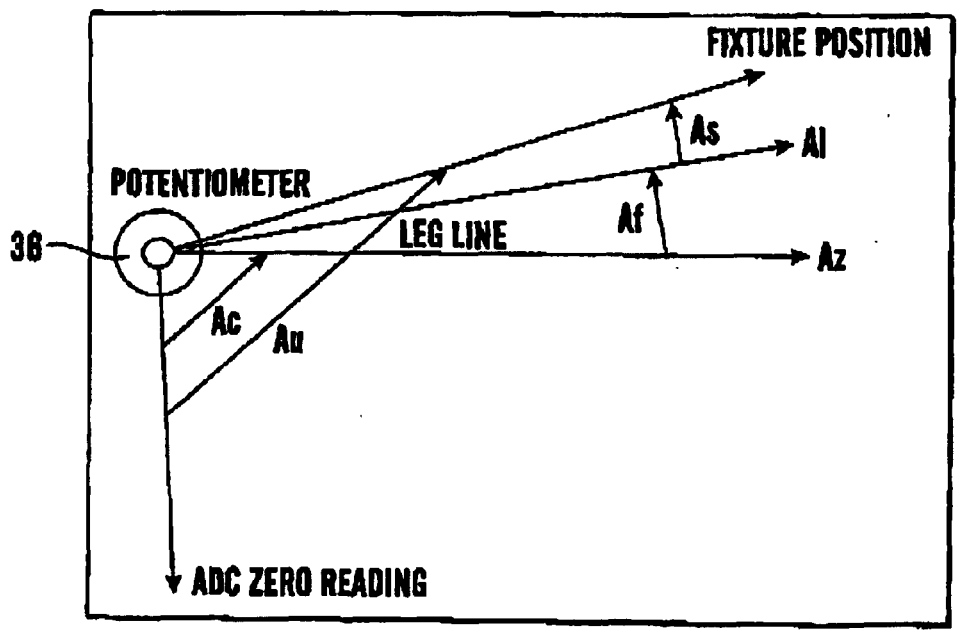
FIG. 4 is a diagram showing how angular measurements are calculated, using the circuitry of FIG. 3.

Referring also to FIG. 4, when the microprocessor reads the uncorrected angle Au, it also reads the correction factor for this angle (as described above) and applies it to the reading Au (typically using a linear interpolation algorithm) to create a corrected reading, Ac.

This angle Ac represents the absolute angle of the planar surface 21 relative to the body of the device. This angle is not suitable for displaying to the user as it does not represent the angle of the foot in a readily understandable format. To produce a reading that represents the angle of the foot in degrees relative to the line of the leg, the fixture is set so that the planar surface 21 is exactly in line with the leg line. At this point, the user (for example the calibrator, or clinician) presses the zero degree reset button 34, as indicated in FIGS. 1 and 2. At this point the microprocessor notes the angle measured (the 'absolute null' denoted by Az, and corrected using the correction data in the EEPROM as before). The relative angle of the planar surface 21 can then be determined by subtracting the corrected angle Ac from the null angle Az. The resulting angle, denoted Af, can therefore be positive or negative and represents the angle of the foot base from the line of the leg.

The user may also want to be able to set a 'local null', A1, at some position other than the 'absolute null', Az. When the planar surface 21 is at the required position, the user re-presses the reset button 34 to obtain a 'local null' reading. Alternatively, a second switch may be provided for this 'local null' reading function. The local angle, denoted by As, is then displayed on the liquid crystal display 32, as indicated in FIGS. 1 and 2, relative to the 'local null' by subtracting Ac from the local null A1. The angle of the planar surface 21 relative to the leg line 'absolute null' Af is also displayed to the user. To ensure that the system retains its settings when the unit is powered down, the local null and absolute null values are stored in the EEPROM 44.

The device may be provided with a communication link to an external computer, to allow transfer of data and/or parameters, for example patient information, patient treatment history, historical data or calibration curves. This link may take the form of a parallel or serial data port. Measurements may then be stored in or transferred from a patient database, for example to be compared with measurements from previous treatment sessions.

Figure 5:
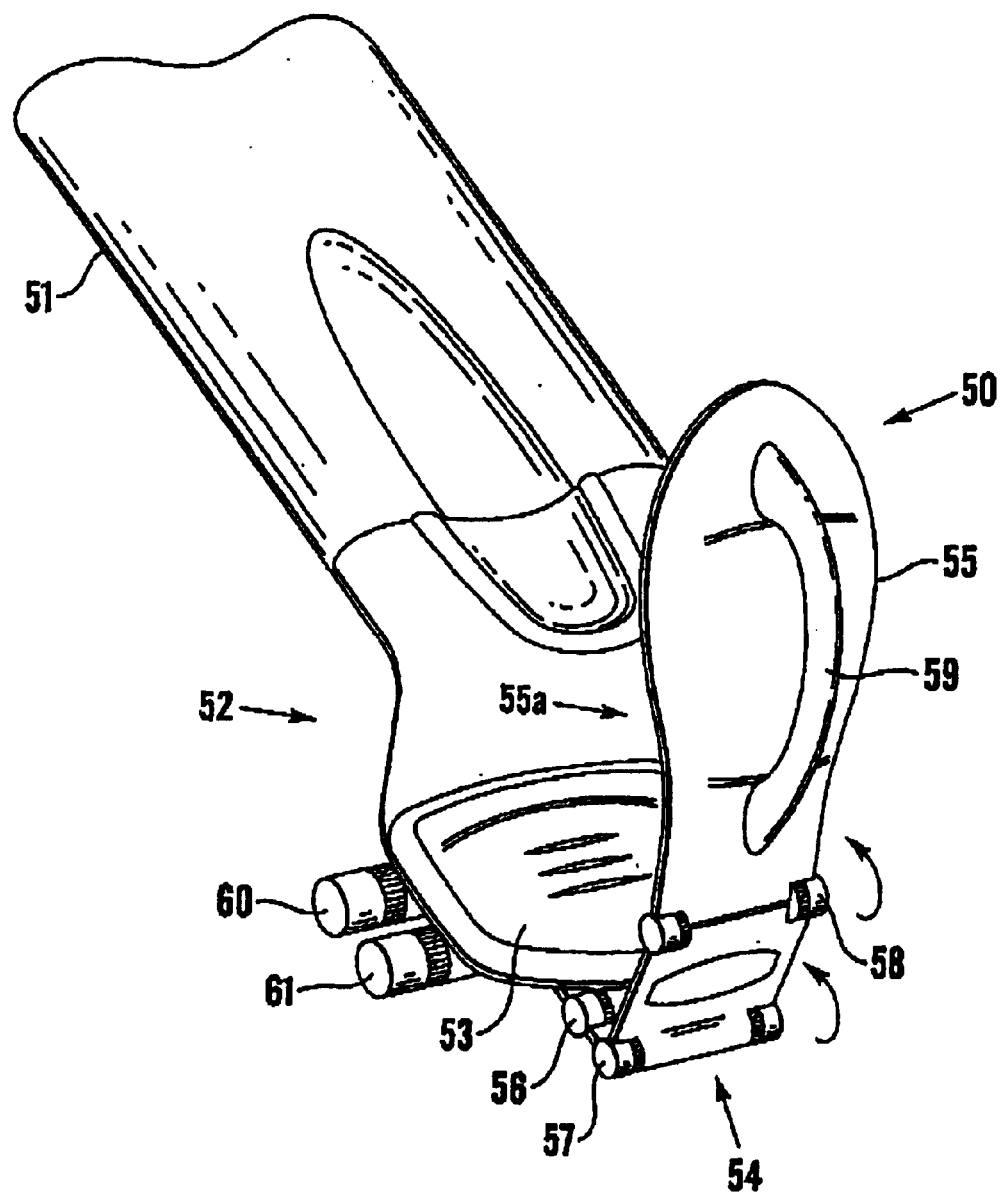
FIG. 5 shows a similar device with a fixed reference point as in FIG. 1 but using a vernier scale for detection of angular tilt.

Turning now to FIG. 5, a device according to this embodiment of the invention is generally designated 50. The device 50 comprises a leg rest 51 which, in use, is placed on the edge of the chair or couch on which the patient sits or lies, the patient's lower leg being supported by the rest 51 with the ankle and foot projecting beyond it. The rest 51 is padded for the patient's comfort.

The rest 51 has a downwardly directed end portion 52 on which a removable tray 53 is received. An articulated platform 54 is pivotally mounted beneath the end portion 52, such that the platform 54 can be rotated about a vertical axis. The platform 54 includes a planar member or casting plate 55, having a planar surface 55a which, in use, is brought into contact with the sole of a patient's foot, generally as described in detail above with reference to FIGS. 1 to 4. Hinges 56, 57, 58 allow movement of the platform 54 about horizontal axes. A handle 59 is fitted to the plate 55 to facilitate manipulation.

Angular movement of the platform 54 about the vertical axis is monitored by means of a Vernier scale on adjustment knobs 60, 61.

The device 50 is used in a broadly similar manner to the embodiment described above. The rest 51 is placed on the patient's chair or couch and the patient's leg placed in position on the rest. The plate 55 and the patient's foot are then manipulated, essentially as described above, the degree of correction being set using the Vernier at 60, 61. The tray 53 collects surplus casting material and is easily removed for cleaning (or may be a completely disposable item).

Figure 6:
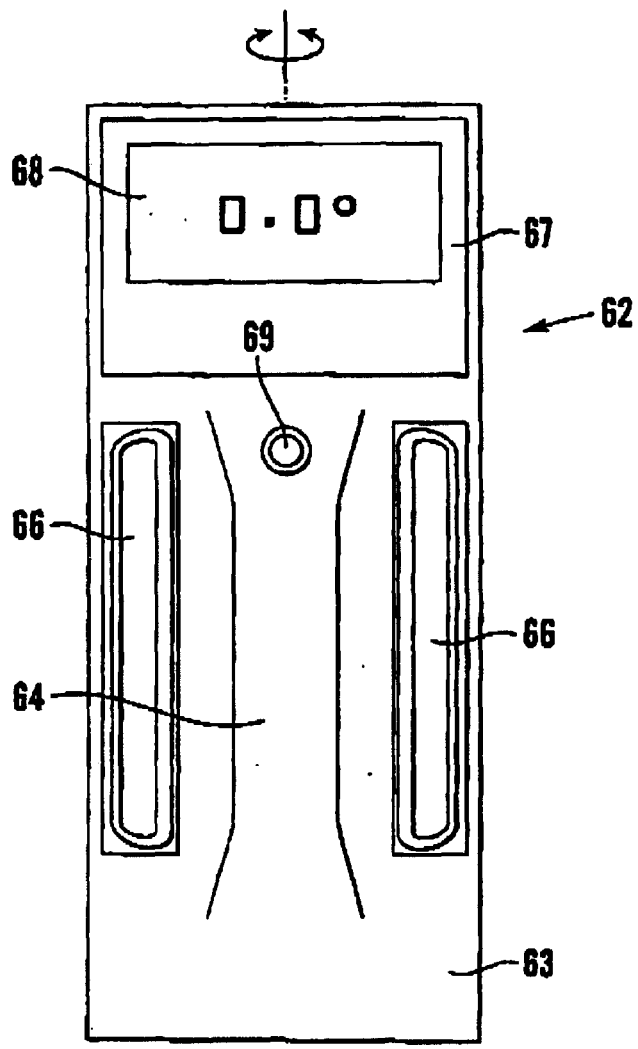
FIG. 6 is a plan view of a further embodiment of a device according to the invention.
Figure 7:
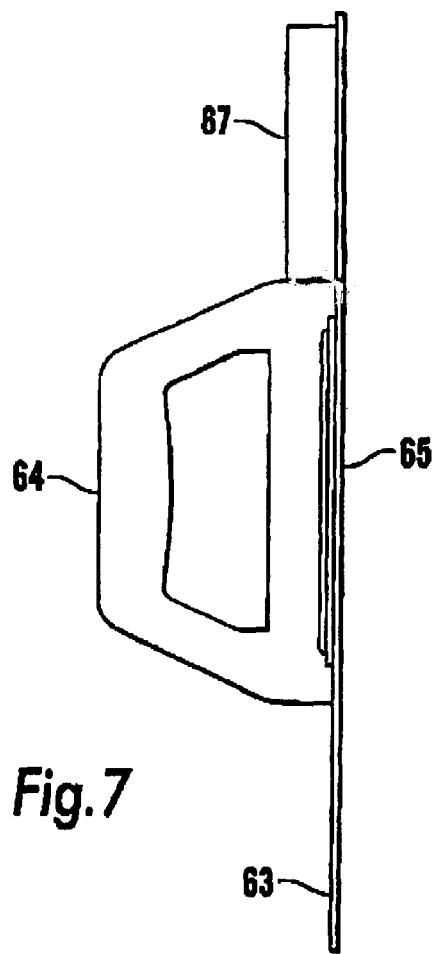
FIG. 7 is a side view of the device of FIG. 6.

Referring now to FIGS. 6 and 7, a hand-held device according to this embodiment of the invention is generally designated 62 and comprises a planar member or casting plate 63 with a handle 64. The plate 63 is a rigid plate of approximate thickness 3 mm having a planar surface 65, and may be formed integrally with the handle 64 e.g. by moulding in plastics material. Two spring-loaded clips 66 are provided laterally of the handle 64, for retaining the edges of a paper towel wrapped around the surface 65 of the plate 63.

Mounted on the plate 63 and (as viewed in FIG. 6) above the handle 64, is an electronics unit 67 which incorporates a means for measuring angular tilt of the plate 63 and surface 65. The unit 67 has a liquid crystal display 68, and a zero reset button 69 is incorporated into the handle 64. The button 69 is operable by the thumb of the user's hand which grasps the handle 64.

The electronics unit 67 includes means for detecting an external reference from which the degree of tilt of the planar surface 65 can be calculated. For example, the electronics unit 68 may include means for detecting magnetic north, and/or a rotational potentiometer which is rotated when the plate 63 is rotated, thereby changing the resistance of the potentiometer. The resultant change in voltage is converted by digital logic circuitry to an output value in degrees which is displayed on the liquid crystal display 68. Alternative means for detecting the tilt of the plate 63 may be provided by a mechanical reference means or by means of a gyroscope.

In order to use the device 60, a clean paper towel is placed against the planar surface 65 of the plate 63 and folded back and inserted under the raised clips 66. A plaster of Paris bandage is applied to the foot in the usual manner, in preparation for the casting position, and the patient told to relax the foot completely as the bandage application is completed.

The planar surface 65 of the plate 63 is then brought into contact with the sole of the patient's foot and the method for taking subtalar joint neutral casts is then carried out, substantially as described above.

Figure 8:
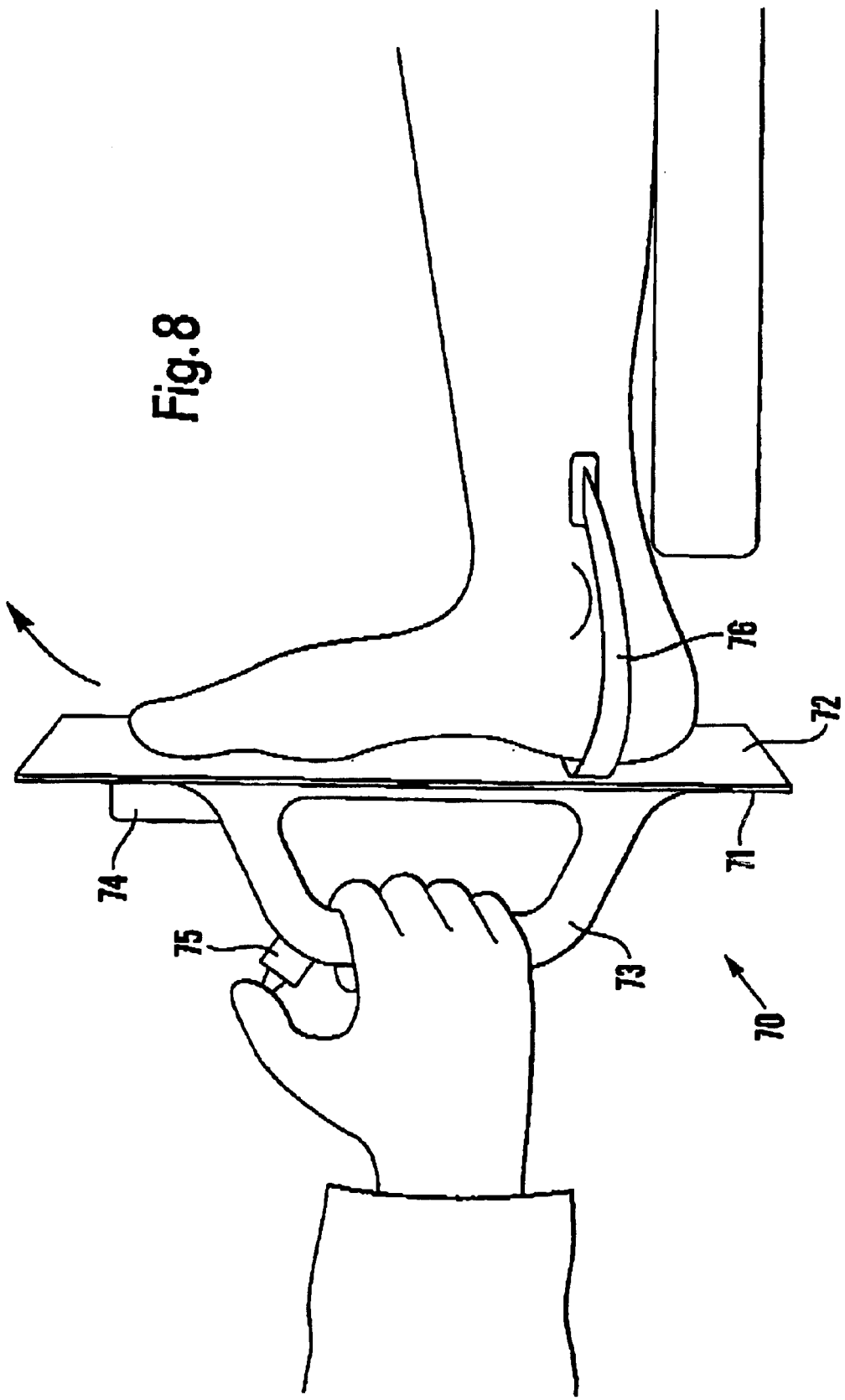
FIG. 8 shows a modified form of the device of FIGS. 6 and 7, in use.

The device of FIG. 8 (generally designated 70) is similar to that described with reference to FIGS. 6 and 7, in that it comprises a casting plate 71 having a planar surface 72, and a handle 73. An electronics unit 74 with an LCD display (not visible) is mounted on the plate 71 above the handle 73, and a reset button 75 is provided to zero the display.

The device 70 differs from that of FIGS. 6 and 7 in that it is provided with a reference arm 76 which is pivotally connected to the plate 71. The free end of the arm 76 bears against the patient's lower leg. The point at which the arm 76 is pivotally connected to the planar surface 72 of the plate 71 includes means (not shown in detail) which is operably linked to the electronics unit 74, by which the angle of the arm 76 relative to the surface 72 can be measured. The arm 76 provides a fixed point relative to which the angle of tilt of the surface 72 can be measured.

Figure 9:
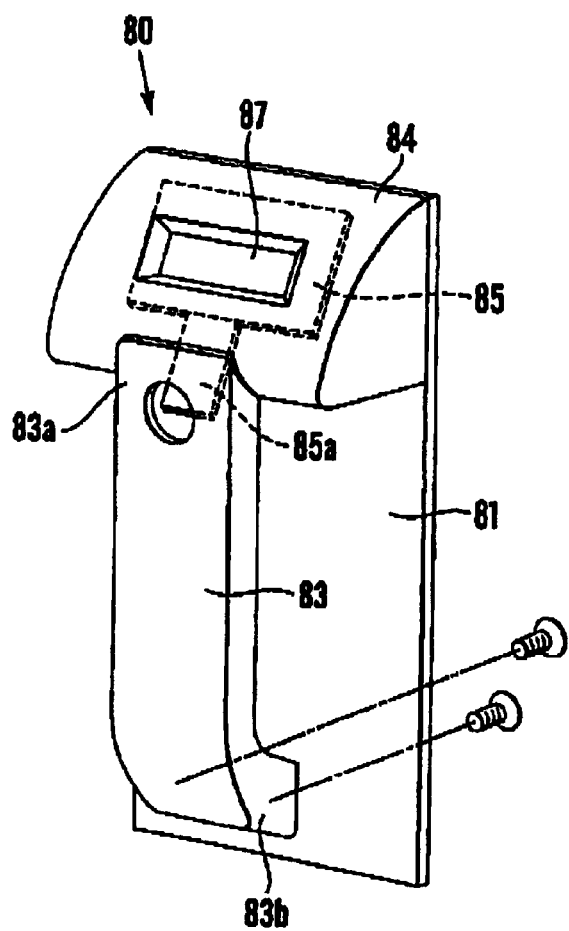
FIG. 9 is a perspective view of another modified form of the device.
Figure 10:
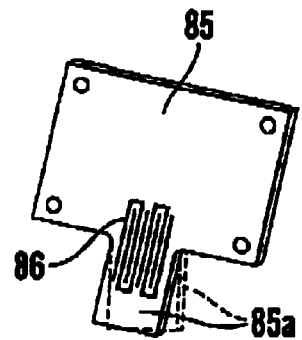
FIGS. 10 & 11 are detail perspective views of parts of the device shown in FIG. 9.
Figure 11:
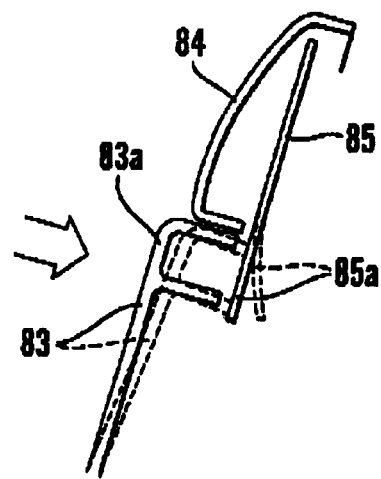

Another form of the device is shown at 80 in FIGS. 9 to 11 in which the planar member or casting plate 81 has a handle 83 secured at one end 83b to the plate 81 whilst the other free end 83a extends towards a lower part of the electronics unit 84. On the manual application of pressure to the handle 83 it yields so that the end 83a contacts a resiliently flexible extension 85a of a printed circuit board 85 in the electronics unit 84. The extension 85a carries a number of strain gauges 86 (FIG. 10) thereon which, on deflection of the extension 85a by the handle 83, produce a signal which is representative of the force applied. This is indicated in the LCD display 87 of the unit 84.

The action of the strain gauges 86 is such that it allows substantially exact repeatability of pressure on the planar surface of the plate 81 against the sole of the foot especially whilst a plaster of Paris bandage or other moulding material sets.

Figure 12:
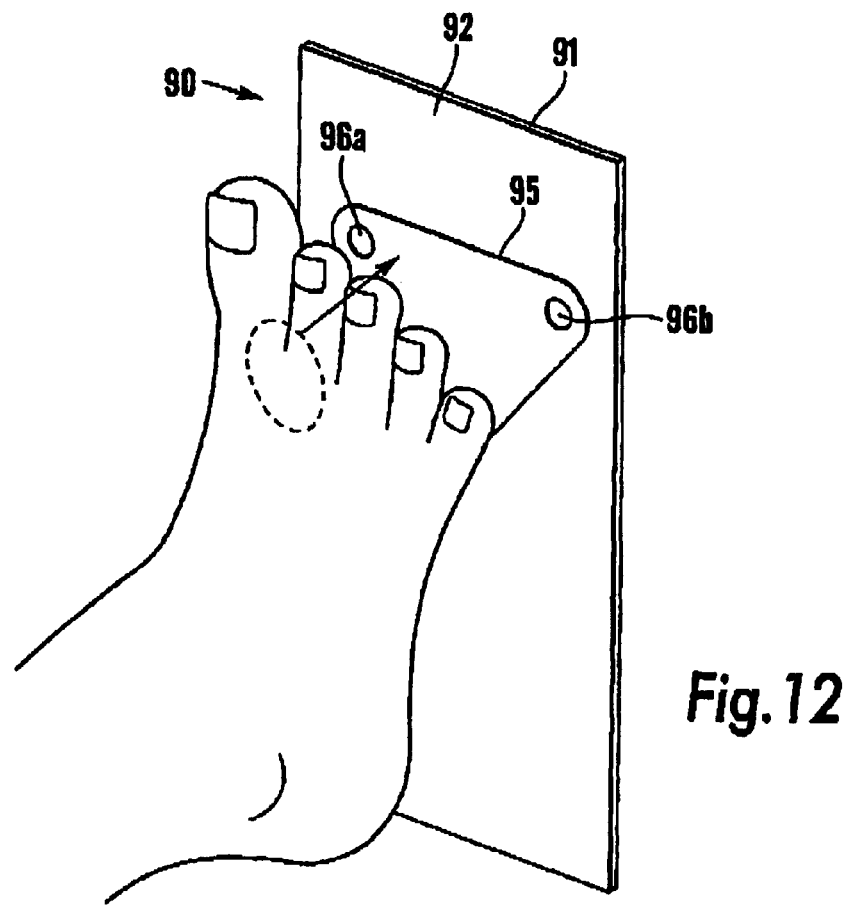
FIG. 12 is a perspective view of a still further form of the device.
Figure 13:
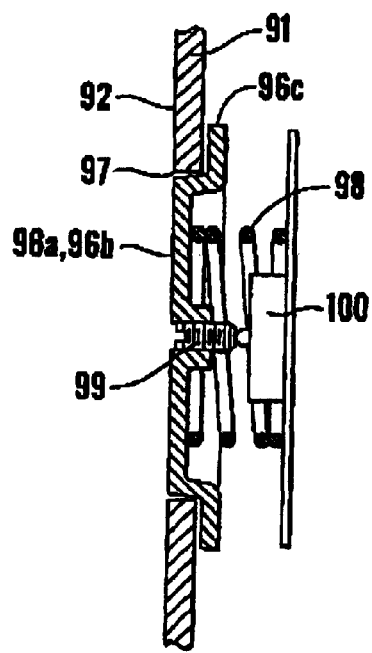
FIG. 13 is a detail cross sectional view on an enlarged scale of one of the micro switch arrangements.

Referring to FIGS. 12 and 13 a further form of the device is shown at 90 in FIG. 12 where the planar surface 92 of the casting plate 91 is provided with a triangular shaped guide line 95, which assists the clinician in positioning the planar surface 92 against the sole of a foot at the fore foot. The plate 91 has two buttons 96a and 96b bounded by the guide line 95 and located in respective holes 97 through the plate 91 (FIG. 13). Each button 96a, 96b is located in its hole 97 by a compression spring 98 and a cranked peripheral flange 96c of the button which bears against the back of the plate 91 about the hole 97. Each button 96a, 96b hs a central adjustment screw 99 which contacts a micro-switch 100 on contact of the button with the sole of the foot.

One button 96a is for use with a right foot (as shown in FIG. 12) and the other button 96b is for use with a left foot. On initial contact of the first metatarsal joint or head of the forefoot sole area with a corresponding button 96a, the latter is depressed into operating contact with the switch 100. When the first metatarsal lifts away from the planar surface 92 the button 96a and its screw 99 will move away from the switch 100 causing a light (not shown) or other indication to be operated to draw the attention of the clinician to the fact that the metatarsal lifting has taken place. Such light may be conveniently situated at the LCD of an electronics unit (not shown) provided on the plate 91 in the manner already described.

This arrangement enables the maximum range of motion of how far the foot inrolls to be measured before the head of the first metatarsal lifts away from the planar surface 92. Thus by placing the planar surface 92 of the plate 91 against the forefoot sole area and putting pressure predominantly on the outer metatarsal heads, the whole forefoot moves out of contact and so measures the angle of pronation.

At the maximum range of motion the head of the first metatarsal will lift away from the corresponding button 96a in the plate 91 so causing illumination of a corresponding indication light.

What is claimed is:

1. A device for use in taking a mould from a foot comprises:

(a) a member having a planar surface on one side, for receiving at least a
   portion of a sole of the foot thereon; and
   (b) operating means provided on the opposite side of the said member to said
   planar surface for operation of the member in the pressure application of the planar surface into contact with the at least portion of the sole, said operating means further providing means for inverting and everting the planar surface of the member while the planar surface is in contact with the at least portion of the sole for inverting and everting the foot and for appropriate support and joint or other location of the sole during the application and setting of molding material to at least the sole of the foot.

2. A device according to claim 1 wherein the said member carries means for measuring and indicating an angle of tilt of the planar surface when one of inverting and everting is applied to the planar surface especially during the application and setting of molding material.

3. A device according to claim 1 wherein the device includes a leg rest for placing on a seat or couch and for receiving and positioning a leg of patient seated on the seat or lying on the couch whereby the foot of the leg extends forwardly from the leg rest, the said member being movably mounted from the leg rest for movement to or from an operative contact position of its planar surface with the sole and for the inverting and everting of said surface relative thereto.

4. A device according to claim 3 wherein the said member is hingedly mounted from the leg rest for movement about a substantially horizontal axis or about more than one such axes for movement to or from an operative contact position of its planar surface with the foot sole and for tilting of said surface relative thereto about the or each horizontal hinging axis.

5. A device according to claim 3 wherein the said member is pivotally mounted from the leg rest for angular movement about a substantially vertical axis for angular side tilting of its planar surface relative to the foot sole when in contact therewith.

6. A device according to claim 5 wherein means is provided for measuring and indicating the angle of angular movement of the said member and its planar surface about the substantially vertical axis.

7. A device according to claim 1 wherein the operating means is arranged to also operate means for measuring and indicating the pressure of application of the said member when the planar surface thereof is in contact with the at least portion of the sole.

8. A device according to claim 1 wherein the said member is provided at its planar surface with depressible means for contact by at least one metatarsal point of a foot sole whereby on lift off of the point from said means the latter is caused to operate switch means controlling indication means for indicating that lift off has taken place.

9. A device according to claim 8 whereon the depressible means comprises at least one spring loaded button and cooperating switch.

10. Method of taking a mould of a foot using a device according to claim 1 comprising:

(a) applying the planar surface of the said member by pressure application to at least part of the sole of a foot suitably positioned for the purpose;

(b) at least one of inverting and everting said member while the planar surface is in contact with the sole for appropriate support and joint or other location of the sole;

(c) applying molding material to at least the sole while so supported;

(d) allowing the molding material to set while the sole is so supported; and (e) withdrawing the planar surface from contact with the sole and effecting removal of the set molding material from the foot.

* * * * *